United States Patent [19]
Navis

[11] Patent Number: 6,000,400
[45] Date of Patent: *Dec. 14, 1999

[54] OPTICALLY TRANSPARENT MEDICAL INSTRUMENT COVER

[75] Inventor: John A. Navis, Naperville, Ill.

[73] Assignee: Janin Group, Aurora, Ill.

[*] Notice: This patent is subject to a terminal disclaimer.

[21] Appl. No.: 08/741,348

[22] Filed: Oct. 29, 1996

[51] Int. Cl.⁶ .................................................. A61B 19/00
[52] U.S. Cl. ............................................ 128/849; 128/856
[58] Field of Search ..................... 128/849–856

[56] References Cited

U.S. PATENT DOCUMENTS

| | | |
|---|---|---|
| 3,037,507 | 6/1962 | Melges ..................... 128/856 |
| 4,392,853 | 7/1983 | Muto . |
| 4,473,073 | 9/1984 | Darnell . |
| 4,522,196 | 6/1985 | Cunningham et al. . |
| 4,634,433 | 1/1987 | Osborne . |
| 4,887,615 | 12/1989 | Taylor . |
| 4,926,851 | 5/1990 | Bulley ..................... 128/856 |
| 5,148,940 | 9/1992 | Mendise . |
| 5,168,863 | 12/1992 | Kurtzer . |
| 5,174,276 | 12/1992 | Crockard . |
| 5,325,846 | 7/1994 | Szabo . |
| 5,433,221 | 7/1995 | Adair ..................... 128/856 |
| 5,490,524 | 2/1996 | Williams ................. 128/856 |

*Primary Examiner*—Michael A. Brown
*Attorney, Agent, or Firm*—Lee, Mann, Smith, McWilliams, Sweeney & Ohlson

[57] ABSTRACT

A multipurpose, flexible cover for medical instruments with a closed-end cover that is optically clear throughout. The transparent cover is used with optical medical instruments such as cameras and lasers. The cover has a closed end that is a homogeneous polyurethane piece folded over itself and sealed along its side edges to form a receptacle to retain the medical instrument. The closed-end portion, which can be associated with a different types of cameras and lasers, is optically clear with surgical clarity.

3 Claims, 2 Drawing Sheets

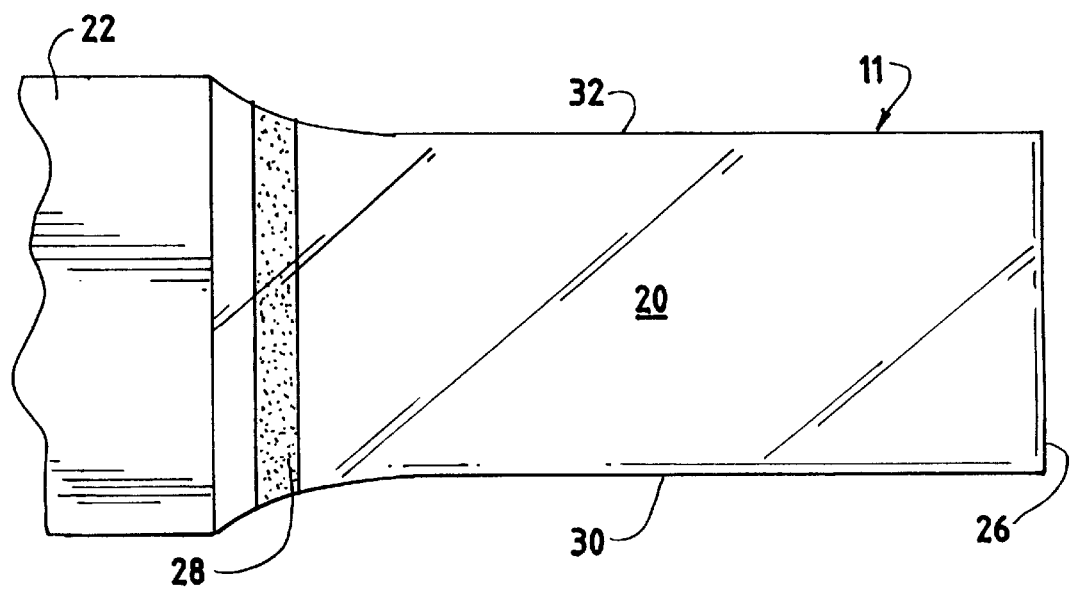

OPTICALLY TRANSPARENT MEDICAL INSTRUMENT COVER

BACKGROUND OF THE INVENTION

The invention generally relates to covers for medical instruments requiring optical transparency. Specifically, the invention entails a multipurpose, closed-end cover that is optically clear with surgical clarity throughout the closed end.

With the wide use of medical instruments that must remain sterile and require unobstructed optical clarity, the present cover provides a means for maintaining sterility and not inhibiting the scene. Use is compatible with different types of cameras, laser equipment, and other optically related instruments. This invention does not require the use of a lens or a special fenestration in the cover for viewing or functioning through.

A large variety of scopes have been developed to serve a physician's different needs during endoscopic surgeries. A surgeon may use several different scopes during one operation. Changing the sterile scope that had been attached to a non-sterile instrument such as a camera will compromise the sterility of the scope and therefore possibly the entire procedure. Others in the industry have provided covers for medical instruments used in endoscopic examinations that allows switching among similar instruments. A closed-end covering, which is embodied in U.S. Pat. No. 4,522,196, was developed that provides a permanent, semi-rigid, optically clear fenestration between the scope eyepiece and the camera lens. The use of a lens requires an extra seal around the lens and a means for implanting that lens into the plastic covering.

U.S. Pat. No. 4,522,196 is directed to a reusable, sterile covering for a surgical camera. The flexible covering is for use in combination with an endoscope and a camera that has a lens-to-endoscope coupling. The coupling temporarily couples the endoscope to the camera. The covering comprises a body portion for covering the camera and an end portion for enclosing the coupling and for defining a barrier by interposition between the camera and endoscope. The end portion is optically clear and made of material that is a rigid or semi-rigid relative to the flexible covering material. The clear end portion fits in the optical path between the endoscope and the camera. This covering is used for the same purpose as the present video camera sterilization embodiment, however, the '196 patent's covering in each embodiment is in combination with an optically clear aperture or member registered in the endoscope-to-camera optical path. In all embodiments, the '196 patent requires that the covering have a clear aperture portion or separate member attached to it or the covering is sealed around the clear portion. The '196 patent does not suggest or teach that the material used for the clear portion would comprise the entire sterile cover or that such a material exists that would be useful for replacement of the covering. It merely suggests that for the aperture, or separate member, that is to be registered in the optical path, a clear plastic film could be used at this portion. The video camera sterilization device of the present invention does not require a means for registering an optically clear aperture or member.

The semi-rigid fenestration of optically clear plastic must be correctly lined up with the eyepiece of the scope and the lens of the video camera for the image to be centered and completely and/or clearly shown on the monitor. The variety of camera sizes may make the fenestration size important for switching among instruments. The plastic film that is attached to the fenestration is somewhat stiff and not transparent. The alignment can be awkward, especially where sterile instruments are initially inserted into the cover during or for a sterile operative procedure.

The previous utilization of a lens or an optical portion construction can preclude clear viewing through the cover if the instrument moves inside the cover. Further, the seal around the lens increases the chance of leakage or other failure. No discovered prior art discloses a single-material, transparent polyurethane closed-end cover portion for a laser or a camera and camera lens coupled to an endoscope. The present application eliminates the separate and/or different material end portion of the cover and uses only a homogenous flexible optically clear, non-static polyurethane to cover the laser or camera lens and the rest of the camera body. The optical clarity can be distorted only by a very narrow seam if the camera or laser is not inserted in the center part of the cover. The cover must be misaligned at least 90° for the seam to affect the image. The foregoing needs also exist in the medical field for other procedures.

Accordingly, it would be desirable to provide a totally clear closed-end cover, which is distortion free for surgical clarity, that can be used to maintain sterility of medical equipment. The present invention has an optically clear closed-end. Any portion of the polyurethane closed-end portion is sufficiently clear for optical use and there is no need to position a lens over the video camera. Moreover, it would be significant in the medical industry to provide a cover that is distortion free to allow accurate viewing of procedures being filmed.

In connection with the foregoing objectives, the chosen polyurethene material is optically clear so that one can see through any portion of the polyurethane closed-end portion with surgical acuity. There is no need to position a lens or specifically formed fenestration over a video camera or laser. Therefore, there is no need for a circular lens to fit over the lens of the camera itself, which abuts the eyepiece of the endoscope. Also, the optically clear, polyurethane, closed-end cover eliminates (1) the need to have a cover with a seal around an attached lens held in the cover, (2) means for implanting the lens in the plastic cover, and (3) the need for means to position a lens in the optical path between scope and camera.

It is a further goal of the invention to provide a cover where the closed-end portion applied to the medical instrument is compatible with lasers. Optical clarity improves the performance of a laser.

It is also a goal of the invention to provide a cover that conforms easily to different camera configurations. The present invention functions with direct in-line scope attachments and with scopes where the camera couplers are perpendicular to the camera. The camera couplers with the scope attached perpendicular to the camera can be used with the present device without concerns of aligning the cover or inserting a new cover because the present closed-end portion is optically clear.

Further, it is another intention of the invention to provide a cover that is supple, pleasant to touch, and durable. The specifications of the preferred components provides these attributes. Other aspects and benefits of the invention will be appreciated by those practicing medicine in each respective additional application of the cover.

SUMMARY OF THE INVENTION

The present invention is a cover primarily for use as a sterile cover that is compatible with multiple instruments including those requiring optical clarity. The closed-end cover portion is optically clear throughout. The closed-end portion is a homogeneous polyurethane piece folded over itself to form a receptacle to retain the medical instrument.

BRIEF DESCRIPTION OF THE DRAWINGS

FIG. 4 shows a side view of the embodiment of FIG. 3 taken along line 7—7;

FIG. 5 discloses a top view of an alternate embodiment.

DETAILED DESCRIPTION OF THE INVENTION

Figure 1:
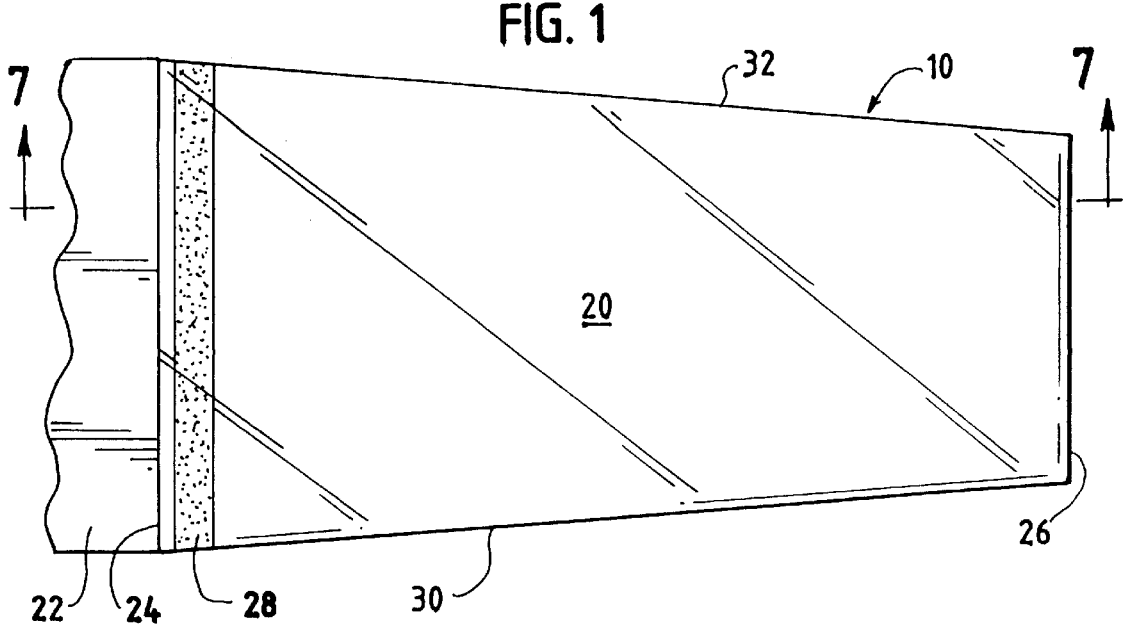
FIG. 1 is a top view of a preferred embodiment.

The invention is a multipurpose, flexible cover for medical instruments with a closed-end portion that is optically clear throughout. The transparent polyurethane closed-end portion is used with endoscopic medical instruments such as cameras and lasers.

In the Figures, like reference numerals indicate the same elements throughout. Reference numerals 10 and 11, respectively denote the basic cover and an exemplary optional alternative of that embodiment.

Figure 2:
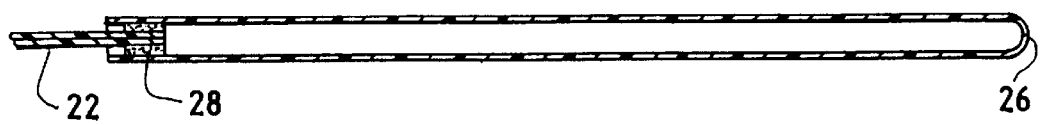
FIG. 2 shows a side view of the embodiment of FIG. 1 taken along line 7—7.

In greater detail, with reference to FIGS. 1 and 2, a cover 10 embodying the invention is illustrated. The cover 10 comprises a closed-end portion 20, an optional hand grip portion 21, and a drape 22 connected at a proximal end 24 opposite to the closed-end portion 20. The closed-end portion 20 and drape 22 are connected at fastening area 28. The closed-end portion 20, which is associated with the camera or laser, is optically clear with surgical clarity.

More specifically, the closed-end portion 20 can be constructed of a polyurethane film that is optically clear and smooth. It must permit the endoscope to rotate during use. The thickness can be from about 1.5 mils (0.0015 inch) to about 6 mils (0.006 inch). About 2 mils has been found to be optimal, being thick enough not to tear and thin enough for easiest use. A commercially available source is J. P. Stevens, Conn, product #1522.

Figure 3:
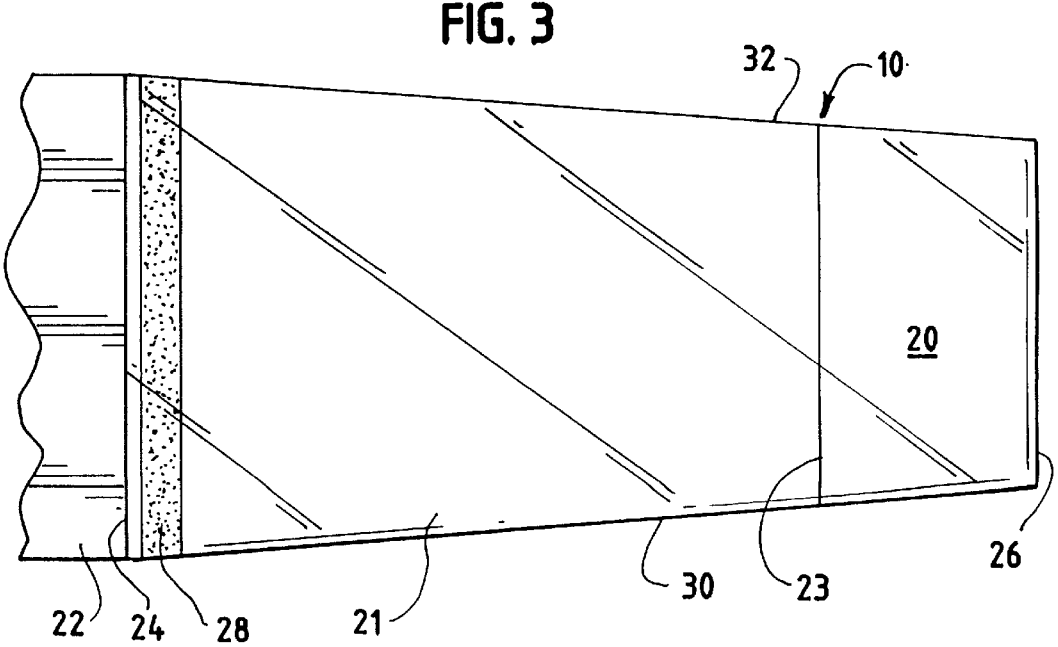
FIG. 3 illustrates a top view of an alternate embodiment with a hand grip portion.

In an optional configuration as shown in FIGS. 3 and 4, a hand grip portion 21 can be attached to the closed-end portion 20 along seam line 23. The attachment at seam line 23 is preferably heat sealed with a wire ribbon seal or equivalent. The hand grip portion 21 is contact clear, and a commercially available source is J. P. Stevens, Conn, product #1400. The closed-end portion 20 is still large enough to completely cover the optically sensitive portion of a medical instrument. The hand grip portion 21 is considered because optically clear film has a tendency to stick to itself. Such sticking makes insertion of the medical instrument more difficult, and this option reduces the surface area that may stick together without sacrificing an optically clear closed-end portion because material such as J. P. Stevens, Conn, product #1400 is less sticky than optically clear film.

The closed-end portion 20 is sealed at edges 30 and 32, the side ends of the folded film. The closed-end portion 20, including hand grip portion 21 if used, forms a compartment by folding a non-static polyurethane sheet, which may consist of optically clear film for the closed-end portion 20 bounded to contact clear film for the grip portion 21, over itself and bonding the side ends. The fold is at a peripheral edge 26 and there is no optical distortion at the peripheral edge 26.

The edges 30 and 32 and grip portion 21 need not be optically clear. Preferably, the edges 30 and 32 can be made with a wire ribbon seal, but may be made with any other style seal. The edges 30 and 32 can alternately be heat sealed having another indication to warn that a camera is misaligned in that area. For example, a color could be introduced in the seal or made with a wider seal so that the camera of the endoscope cannot be incorrectly aligned.

The homogeneous polyurethane film folded over itself forms a receptacle inside the edges 30 and 32 to retain a medical instrument. The peripheral edge 26 is the intended location for full insertion of a medical instrument.

In the preferred embodiment shown in FIG. 1, the closed-end portion 20 is tapered so that peripheral edge 26 is narrower than fastening area 28. This permits a medical instrument to be inserted and guided towards the peripheral edge 26. The sides 30 and 32 are shown here as tapered, but they may also be converging at that peripheral edge 26 so it is functionally a "point" configuration.

The drape 22 can be made of a flat tube of varying widths and the desired length. In the preferred embodiment, the drape 22 is an extruded tube, or it may be a flat film folded over itself and sealed on one side. Alternately, the drape 22 can be made of two pieces of flat film of affixed together. The drape 22 can be a semi-translucent material. The drape can be made of non-static polyethylene that is 1.5 mils to 4 mils thick, preferably approximately 2 mil thick. The drape is a tube for enclosing wires or cable extending from the medical instrument.

The proximal end 24 opposite the closed-end portion 20 and the drape 22 can be heat sealed if the films are compatible or adhered by double face tape if the films are incompatible. Such tape is preferred in fastening a polyurethane closed-end portion and a polyethylene drape. There are a wide variety of medical grade double face tapes acceptable for such use. The correct type to use depends on the specific properties of the film that is used.

FIG. 5 provides an optional non-tapered construction of the closed-end portion 20. The embodiment for the cover 10 shown in FIG. 1 is similar to cover 11 of FIG. 5, except that the tapering occurs near the fastening area 28.

Alternate Embodiments

The exact dimensions or proportions of the preferred embodiment and the alternate embodiment are not critical to the invention. The structure and size of the cover can be made to the dimension required for a particular instrument or a particular application. It will also be appreciated that although the invention has been disclosed with reference to a covers for cameras and lasers, it encompasses covers for similar optical instruments. Further, an entire family of covers can be produced based on the disclosed structure and technology.

Achievements

Accordingly, an improved closed-end cover that is optically clear throughout the area to be associated with medical instruments is disclosed herein. While the invention has been described in connection with preferred embodiments for the cover, a range of equivalents are encompassed in the scope of the claims appended hereto.

What is claimed is:

1. A transparent, closed-end cover for medical instruments with optical functions comprising a proximal end and a homogenous closed-end portion that is optically clear and a drape fastened to the closed-end portion wherein the drape is constructed of non-static polyethylene and the closed-end portion is constructed of non-static polyurethane.

2. A transparent, closed-end cover for medical instruments with optical functions; the cover comprising:

- a homogenous, non-static, polyurethane closed-end portion that is optically clear; the closed-end portion is folded at a peripheral edge so that there is no optical distortion along the peripheral edge; the closed-end portion having side edges formed from the folded closed-end portion wherein the side edges are sealed; the peripheral edge and the side edges forming a receptacle to hold the medical instrument; a proximal end opposite to the closed-end portion for inserting the medical instrument into the closed-end portion; and
- a non-static polyethylene drape fastened to the proximal end; the drape forming a tube to enclose wires or cable extending from the medical instrument.

3. The cover of claim 2 wherein the drape is an extruded, seamless tube.

* * * * *

UNITED STATES PATENT AND TRADEMARK OFFICE
CERTIFICATE OF CORRECTION

PATENT NO. : 6,000,400
DATED : December 14, 1999
INVENTOR(S) : John A. Navis

It is certified that error appears in the above-identified patent and that said Letters Patent is hereby corrected as shown below:

Title page item
"Notice: This patent is subject to a terminal disclaimer." is deleted.

In the Abstract, Line 8, after "with" delete "a".

Column 2, Line 32, change "polyurethene" to --polyurethane--.

Column 2, Line 60, amend "provides" to --provide--.

Column 4, Line 16, amend "towards" to --toward--.

Column 4, Line 27, amend "mil" to --mils--.

Column 4, Line 51, delete "a".

Signed and Sealed this

Thirtieth Day of January, 2001

Attest:

Attesting Officer

Q. TODD DICKINSON

Director of Patents and Trademarks